United States Patent

Theis et al.

(10) Patent No.: US 6,605,192 B1
(45) Date of Patent: *Aug. 12, 2003

(54) METHOD FOR PRODUCING HIGHLY PURE MONOETHYLENE GLYCOL

(75) Inventors: Gerhard Theis, Maxdorf (DE); Till Adrian, Bobenheim-Roxheim (DE); Bernd Bessling, Grünstadt (DE); Hans Hasse, Kaiserslautern (DE); Frans Vansant, Kalmthout (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/787,616
(22) PCT Filed: Sep. 21, 1999
(86) PCT No.: PCT/EP98/06968
§ 371 (c)(1), (2), (4) Date: Mar. 20, 2001
(87) PCT Pub. No.: WO00/17141
PCT Pub. Date: Mar. 30, 2000

(30) Foreign Application Priority Data

Sep. 23, 1998 (DE) .......................... 198 43 697

(51) Int. Cl.[7] .............. B01D 3/38; B01D 3/42; C07C 29/80; C07C 31/20
(52) U.S. Cl. ................ 203/3; 203/18; 203/78; 203/79; 203/80; 203/99; 203/DIG. 19; 568/868; 568/916
(58) Field of Search .......... 203/18, 91, 87, 203/73; 568/867, 868, 916

(56) References Cited

U.S. PATENT DOCUMENTS

| | | | | |
|---|---|---|---|---|
| 3,875,019 A | | 4/1975 | Cocuzza et al. ............... 203/18 |
| 4,182,659 A | * | 1/1980 | Anwer et al. ............... 203/18 |
| 4,349,417 A | | 9/1982 | Rebsdat et al. ............... 203/33 |
| 4,622,104 A | | 11/1986 | Neel et al. ............... 203/18 |
| 5,635,590 A | * | 6/1997 | Rink et al. ............... 203/82 |
| 5,738,417 A | * | 4/1998 | Foral ............... 203/18 |
| 6,133,489 A | | 10/2000 | Mohr et al. ............... 568/914 |

FOREIGN PATENT DOCUMENTS

| CA | 1 330 350 | 6/1994 |
|---|---|---|
| DE | 1 942 094 | 2/1970 |
| DE | 2 364 151 | 7/1974 |
| DE | 33 38 488 | 5/1984 |
| DE | 196 02 116 | 7/1997 |
| EP | 0 032 665 | 7/1981 |
| GB | 1 257 558 | 12/1971 |
| JP | 60089439 | 5/1985 |

OTHER PUBLICATIONS

Ullmann's Encyclopedia of Industrial Chemistry 4th Ed. vol. 3 pp. 200–210.

* cited by examiner

Primary Examiner—Virginia Manoharan
(74) Attorney, Agent, or Firm—Keil & Weinkauf

(57) ABSTRACT

A process for the distillative recovery of high purity monoethylene glycol from the hydrolysis, product of ethylene oxide by pressure dewatering, preferably in a battery, vacuum dewatering and subsequent purifying distillation, wherein during the vacuum dewatering an aqueous stream is withdrawn which contains-monoethylene glycol in a concentration below 1% by weight, preferably below 0.1% by weight, medium boilers and low boilers. The withdrawn aqueous stream is, optionally after further workup, removed from the system.

20 Claims, 5 Drawing Sheets

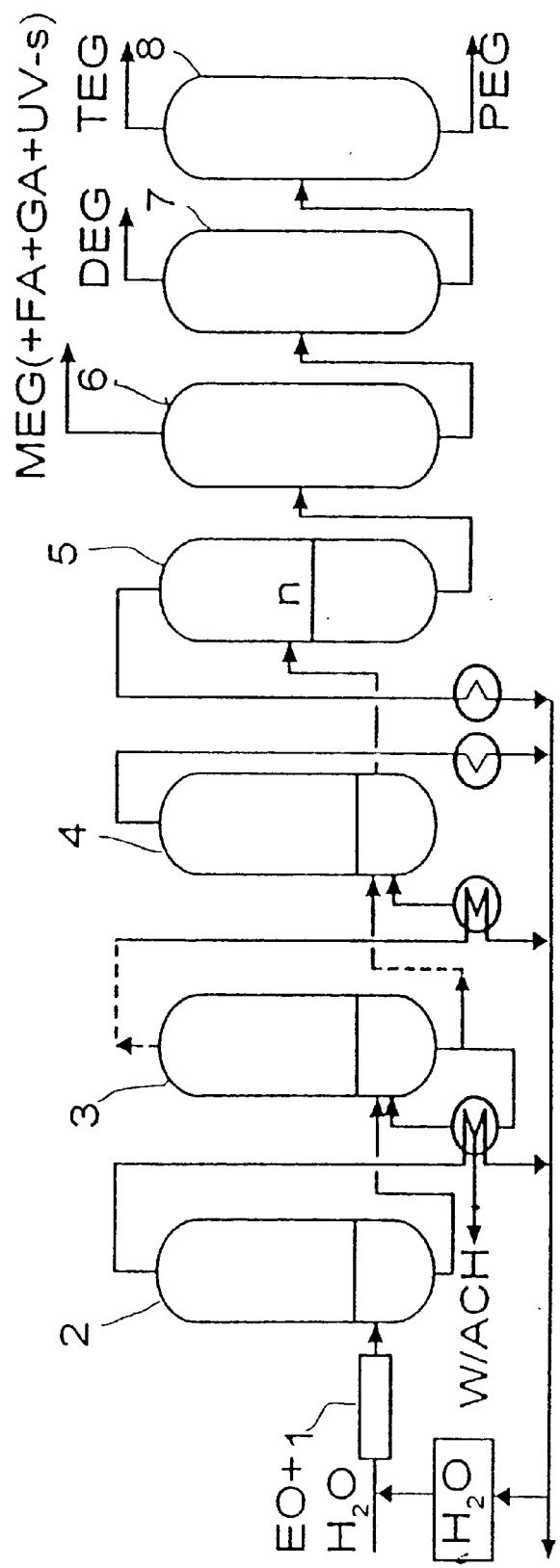
FIG. 1 - Prior Art

METHOD FOR PRODUCING HIGHLY PURE MONOETHYLENE GLYCOL

This invention relates to a process for producing high purity monoethylene glycol. Monoethylene glycol is industrially produced by hydrolysis of ethylene oxide, dewatering and purifying distillation. To improve the selectivity of the ethylene oxide (hereinafter abbreviated to EO) hydrolysis, the hydrolysis reactor is operated using a large excess of water (water:EO weight ratio=4:1 to 15:1). This makes it possible to suppress the fraction of higher glycols, especially diethylene glycol, triethylene glycol, etc. The hydrolysis reactor is customarily operated at temperatures of 120 to 250° C. and pressures of 30–40 bar. The hydrolysis product is initially dewatered, to a residual water content of 100–200 ppm, and then separated into the various glycols in pure form.

The dewatering is generally carried out in a battery of pressure-graduated columns, with decreasing pressure. For heat integration reasons, generally only the bottoms reboiler of the first pressure column is heated with external steam, whereas all the other pressure columns are heated with the vapors from the preceding column. The feed enters each column at a point below the first plate, since no stripping section is required to separate water and glycols. Depending on the water content of the hydrolysis reactor effluent and on the pressure/temperature level of the external steam used in the first column's bottoms reboiler, the pressure dewatering battery comprises from 2 to 7 columns. The pressure dewatering stage is followed by a vacuum dewatering stage, which generally takes place in a column equipped with a stripping section. The water obtained from the dewatering is returned to a point upstream of the hydrolysis reactor. The dewatered glycol mixture is separated into the pure materials in a plurality of columns. Monoethylene glycol, diethylene glycol and triethylene glycol are each withdrawn as top-of-column product, while all other higher glycols are obtained in the form of a mixture known as polyethylene glycols as the bottom product of the last column.

Conventional glycol plants, in addition to the product streams, customarily have only a further single outlet, the acetaldehyde purge at the bottoms reboiler of the second pressure dewatering column. There, the uncondensed fraction of the first column's vapors used for heating is removed from the system. Thus, secondary components, either carried into the glycol plant by the water/EO stream or formed in the glycol plant as a consequence of secondary reactions, can only be removed from the system via the acetaldehyde purge or via the product streams. The latter impairs product quality and so is undesirable.

Hitherto, glycol plants were optimized only with regard to their principal functions, especially with regard to energy and capital costs reduction for the dewatering and purifying distillation. Of late, increasingly tougher requirements are being placed on the product quality of monoethylene glycol, especially with regard to the level of secondary components. There are two monoethylene glycol product qualities: technical grade (antifreeze grade) with lower purity requirements, for use as coolant, and fiber grade, with strict requirements, for use in fiber manufacture, for example. The exact specification of fiber grade varies with the customer, but for free aldehydes, reckoned as acetaldehyde, spectrophotometrically assayed as blue MBTH complex, it generally envisages the range from 7 to 20 ppm and for the minimum UV transmission it generally envisages 76%–80% at 220 nm and 90%–95% at 275 nm. The contributors to the free aldehydes measurement are in particular formaldehyde, acetaldehyde and glycolaldehyde. The UV-active substances, known as UV spoilers, are largely unknown, but are specification-destructive even in concentrations of less than 1 ppm. Examples are acrolein and crotonaldehyde.

JP-A-60,089,439 describes a process for purifying glycol by vacuum distillation with a supply of inert gas. The nitrogen stream strips out a portion of the secondary components to leave a high purity glycol which is suitable for fiber manufacture. However, the process has the disadvantage that large amounts of nitrogen are needed for effective removal of secondary components. This leads to undesirable product losses in the exit gas and to an excessively large fluid-dynamic stress on the distillation column.

DE-A-1 942 094 describes a process for purifying monoethylene glycols by steam distillation in a stripping column, the steam increasing the volatility of the impurities with regard to monoethylene glycol.

CA-C-1330350 describes a process for purifying monoethylene glycol by addition of bisulfite ions and subsequent treatment with anion exchange resins.

There are also purification processes for monoethylene glycol where the formation of secondary components is said to be reduced by special measures in the area of apparatus construction and the materials of construction used for the apparatus. DE-A-19 602 116 describes a purification process for monoethylene glycol in an apparatus whose surface has been treated with reducing phosphorus compounds.

However, the abovementioned processes have the disadvantage of requiring additives or additional equipment-based measures to recover high purity monoethylene glycol.

It is an object of the present invention to provide a simple distillative process for recovering high purity monoethylene glycol, without the use of additives or of specific materials of construction. Specification-destructive secondary components are to be removed from the system in predominantly aqueous waste streams having glycol contents of not more than 1% by weight and the secondary components in the waste streams are to be concentrated by a factor of 10–100, since too much wastewater is produced otherwise.

We have found that this object is achieved by a process for the distillative recovery of high purity monoethylene glycol from the hydrolysis product of ethylene oxide by pressure dewatering, preferably in a battery, vacuum dewatering and subsequent purifying distillation, which comprises withdrawing during the vacuum dewatering an aqueous stream which contains monoethylene glycol in a concentration below 1% by weight, preferably below 0.1% by weight, medium boilers and low boilers and which, optionally after further workup, is removed from the system.

Particular preference is given to a process in which, in addition to the abovementioned solution, the pressure dewatering takes place in a dewatering column having a stripping section with at least one separating stage, preferably with from 2 to 10 separating stages, particularly preferably with from 3 to 6 stages, and in which a portion of the overhead stream of the dewatering column(s) having a stripping section is removed from the system.

It was determined that removal of specification-destructive secondary components is particularly effective at certain locations in the process. Identifying these locations in the process is not a trivial matter, since the complex phase equilibria have hitherto made it impossible to arrive at a sufficiently confident assessment of the behavior of the secondary components. For this reason, conventional large industrial processes have only a very coarse outlet for extremely low boiling secondary components, the acetaldehyde purge at the bottoms reboiler of the second pressure dewatering column. This outlet is not optimized, since the behavior of the secondary components was largely unknown and was not taken into account at the process design stage.

The components are herein subdivided into three classes with regard to their boiling range:
1. low boilers, having a volatility greater than that of water (especially acetaldehyde, formaldehyde in pure water, acrolein), 2. medium boilers, having a volatility between that of water and monoethylene glycol (especially formaldehyde in glycol-containing aqueous solutions, formaldehyde in anhydrous monoethylene glycol, glycolaldehyde, crotonaldehyde), and
3. high boilers, having a lower volatility than monoethylene glycol (especially relatively high molecular weight aldehydes, UV spoilers).

The vacuum dewatering of the invention comprises withdrawing an aqueous stream which contains less than 1% by weight of monoethylene glycol, medium boilers and low boilers, which, optionally after further workup, is removed from the system.

The vacuum dewatering can take place in a vacuum dewatering column, in which case an aqueous stream of medium boilers and low boilers is withdrawn as a sidestream. The vacuum dewatering column is fed with a stream comprising 1–99% by weight, preferably 50–90% by weight, of monoethylene glycol, 1–99% by weight, preferably 50–10% by weight, of water and specification-destructive secondary components within the range from 1 ppm to 5%, preferably within the range from 1 ppm to 1%, particularly preferably within the range from 1 ppm to 1000 ppm. The vacuum dewatering column is then operated in such a way as to produce a top-of-column product consisting predominantly of water and having a monoethylene glycol content of below 5% by weight, preferably below 1% by weight, preferably below 1000 ppm, and a base-of-column product consisting predominantly of glycol and having a water content of below 5% by weight, preferably below 1% by weight, particularly preferably below 1000 ppm. The vacuum dewatering column has withdrawn from it a sidestream which is substantially free of monoethylene glycol, i.e., with a monoethylene glycol content of below 5% by weight, preferably below 1% by weight, particularly preferably below 1000 ppm, and enriched with specification-destructive secondary components, especially medium boilers and also low boilers. The dewatering column is operated with a base-of-column temperature of not more than 220° C., preferably from 120° C. to 200° C., particularly preferably from 160° C. to 180° C.

The feed to the vacuum dewatering column is generally the base-of-column effluent from the pressure dewatering column or the last column of the pressure dewatering battery. In individual cases, however, it is also possible to feed the vacuum dewatering column directly with the effluent from an EO hydrolysis reactor. The base-of-column product of the vacuum dewatering column is substantially water-free and is fed to the monoethylene glycol purifying distillation. The top-of-column product, substantially monoethylene glycol-free water, is wholly or partly further used in the process, particularly fed to the hydrolysis reactor. The sidestream can be discharged into the wastewater or be further worked up.

In a further preferred embodiment, two vacuum dewatering columns are connected in series. The glycol-containing stream to be purified is fed to the first vacuum dewatering column. The base-of-column product of the first vacuum dewatering column is fed to a second vacuum dewatering column, preferably into the middle section thereof. Typical glycol concentrations in the bottom product of the first vacuum dewatering column are 70–99.5% by weight, preferably 85–99.5% by weight, particularly preferably 95–99% by weight. The head product withdrawn from the second vacuum dewatering column is an aqueous, substantially glycol-free stream which has a glycol content of below 5% by weight, preferably below 1% by weight, particularly preferably below 1000 ppm and is rich in medium boilers and also low boilers. The bottom product of the second vacuum dewatering column is substantially anhydrous glycol; it is fed to the monoethylene glycol purifying distillation. The base-of-column temperatures in the vacuum dewatering column(s) should generally not exceed 220° C., preference being given to the range from 120° C. to 200° C. and particular preference to the range from 160° C. to 180° C.

It is particularly advantageous to supply the middle section of the only or last vacuum dewatering column with a overhead stream from the monoethylene glycol purifying distillation. This measure makes it possible to remove from the system even secondary components which are formed as a consequence of secondary reactions in the monoethylene glycol purifying distillation. The overhead stream is advantageously small, especially within the range from 1 to 10%, based on the pure monoethylene glycol stream. To minimize the overhead stream to be recycled, the secondary components in the overhead stream have to be concentrated. This requires additional separating stages between the point of removal of the pure monoethylene glycol (side takeoff) and the stream to be recycled; that is, some separating stages have to be disposed between the top-of-column takeoff and the monoethylene glycol sidetakeoff in the monoethylene glycol purifying distillation column, preferably from 1 to 10, particularly preferably from 3 to 6, separating stages. An advantageous side-effect of concentrating and recycling the secondary components is that the small amounts of water present in the column feed to the monoethylene glycol purifying distillation are returned into the vacuum dewatering. This provides a monoethylene glycol having an extremely low water content.

In a particularly advantageous version of the process, the removal of secondary components, especially low boilers, in the pressure dewatering stage is improved as well as the removal in the vacuum dewatering stage. To this end, the pressure dewatering column or at least the first pressure dewatering column of the battery has a stripping section with at least one separating stage, preferably with from 2 to 10 separating stages, particularly preferably with from 3 to 6 stages, and a portion of the overhead stream of the dewatering column(s) having a stripping section is removed from the system.

Conventional large industrial processes utilize an acetaldehyde purge at the bottoms reboiler of the second pressure dewatering column: this is where the vapors of the first pressure dewatering column are substantially condensed, with the uncondensed fraction, about 1–5% by weight of total vapors, being removed from the system. The remaining vapors may, if desired, be postcondensed in a further heat transferor, and the heat of condensation may be utilized at a suitable location in the overall process. However, this conventional solution will remove via the acetaldehyde purge only secondary components which leave the first pressure dewatering column as part of the vapors. This is inadequate in the case of formaldehyde in particular, since the volatility of formaldehyde in aqueous glycol solutions decreases with increasing glycol content, especially as a consequence of chemical reactions of the formaldehyde with water and glycols. So as to separate formaldehyde from the glycol-containing bottom product of the pressure dewatering column, the pressure dewatering column or at least the first pressure dewatering column of a battery requires a stripping section of at least one stage, preferably from 2 to 10 stages, particularly preferably from 3 to 6 stages. Only when the formaldehyde has been removed into the purely aqueous vapors of the first column can it be purged from the system together with acetaldehyde. The efficiency of removal of the formaldehyde in the stripping section improves with the temperature and correspondingly the pressure in the pressure dewatering column, or in the first pressure dewatering column of the battery, and with the water content of the reactor effluent. Two of the additional plates in the stripping section can be saved if the bottoms reboiler is constructed as a "divided base" as described in DE-C-33 38 488.

The amount of secondary components, especially acetaldehyde or formaldehyde, removed from the system depends on the amount of wastewater removed. It has to be borne in mind, however, that the amount of vapor not condensed in the bottoms reboiler of the second dewatering column cannot be increased ad infinitum for reasons of the integrated energy system and on account of control-engineering restraints. The inventors have found a particularly preferred version of the process, whereby further removal of secondary components from the condensed vapor is possible by steam stripping. The stripping steam loaded with secondary components can subsequently be utilized for its energy content at a suitable location in the process. Steam stripping, therefore, requires no additional energy, only an additional apparatus. The removal of secondary components from the system is particularly effective when the effluent from the stripper is refluxed into the first dewatering column, since this recycling will increase the aldehyde content at the top of the first pressure dewatering column and in the stripper and hence also the removal rate.

Advantageously, the temperature below the feed point into the pressure dewatering column is above 80° C., but preferably within the range from 100° C. to 250° C., particularly preferably within the range from 115° C. to 230° C., the pressure in the stripping section being not less than 1 bar, preferably within the range from 2 to 30 bar.

Advantageously, the overhead stream of the pressure dewatering column(s) having a stripping section is introduced into a partial condenser and/or a stripper, especially a steam stripper, and the gaseous stream(s) enriched with secondary components is (are) removed from the system.

Suitably, the partial condenser and/or the stripper are operated at above 90° C., preferably at from 120° C. to 250° C.

BRIEF DESCRIPTION OF THE DRAWINGS

Embodiments of the invention will now be more particularly described by way of example with reference to a drawing, where FIG. 1 shows a scheme for a large industrial process for glycol recovery according to the prior art, FIG. 1a corresponds to FIG. 1 and illustrates the removal of the aqueous stream as a sidestream from a single vacuum dewatering column in accordance with a first embodiment of the improved process.

FIG. 1 shows a scheme for the large industrial recovery of glycol according to the prior art. A water/ethylene oxide mixture having a water:ethylene oxide weight ratio of from 4:1 to 15:1 is fed to the hydrolysis reactor 1 and then to a pressure dewatering stage, herein depicted as a battery of three pressure-graduated columns 2, 3 and 4. The feed point for the columns 2, 3 and 4 is located in the bottom region in each case. The vapor stream from the first pressure dewatering column 2 is condensed in the bottoms reboiler of the second pressure dewatering column 3 and the uncondensed fraction is removed from the system as so-called acetaldehyde purge (W/ACH, i.e., water/acetaldehyde). The condensed vapors from the pressure dewatering columns 2, 3 and 4 are returned to a point upstream of the hydrolysis reactor 1. The bottom stream from the last pressure dewatering column 4 is introduced into the middle section of a vacuum dewatering column 5. The predominantly water-containing vapor from the vacuum dewatering column 5 is likewise condensed and returned to a point upstream of the hydrolysis reactor 1. The bottom effluent from the vacuum dewatering column 5 is fed to a monoethylene glycol purifying distillation column 6, from where monoethylene glycol plus secondary components, especially formaldehyde (FA), glycolaldehyde (GA) and UV spoilers (UV-S), are withdrawn as top product. The bottom effluent from the monoethylene glycol purifying distillation column 6 is fed to a diethylene glycol purifying distillation column 7, from which pure diethylene glycol is withdrawn as top product and whose bottom effluent is fed to a further column, the triethylene glycol purifying distillation column 8. The top product from the triethylene glycol purifying distillation column is pure triethylene glycol and the bottom effluent from the column 8 contains a mixture of higher glycols, known as polyethylene glycol (PEG).

FIG. 2, in contrast, shows a large industrial process for recovering high purity hylene glycol according to the invention. Compared with the process scheme of FIG. 1; the feed is introduced into the first pressure dewatering column 2 at a higher point along the length of this column, and this pressure dewatering column 2 has a stripping section of from 2 to 6 plates.

Figure 1A:
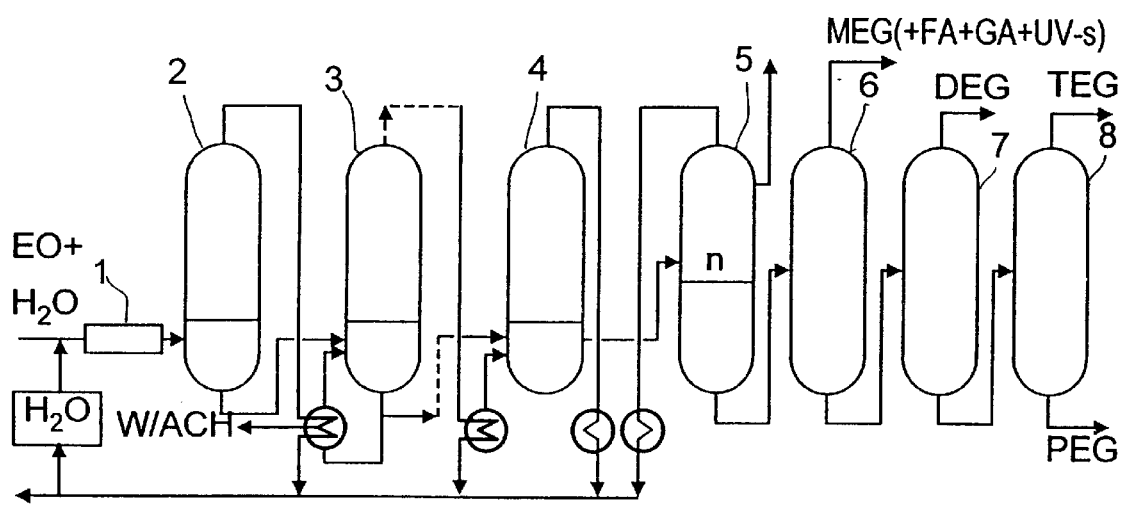
FIG. 1a illustrates how; the industrial recovery of glycol according to the prior art which is shown in FIG. 1 is adapted to realize a first embodiment of the improved process. In accordance with FIG. 1a one vacuum dewatering column (5) is used and the aqueous stream which comprises monoethylene glycol in a concentration below 1% by weight, and additionally medium boilers and low boilers, is withdrawn as a sidestream from the dewatering column (5).
Figure 2:
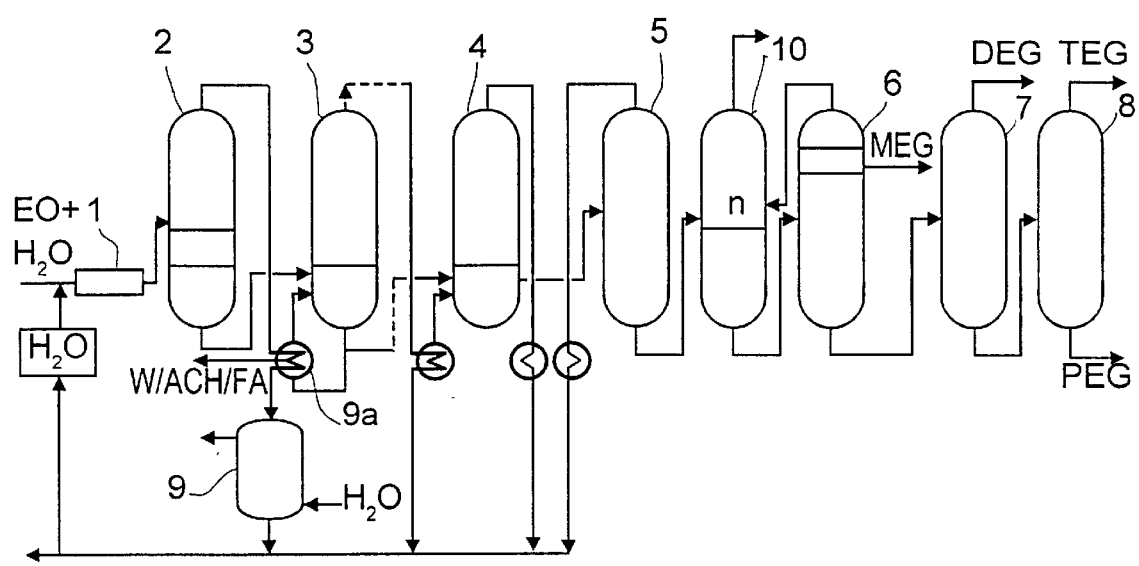
FIG. 2 shows a scheme of a particularly preferred process for glycol recovery according to the invention.

A further difference to the process of FIG. 1 is that the vapor from the first pressure dewatering column 2, following a partial condensation in the bottoms reboiler of the pressure dewatering column 3, is steam-stripped free of secondary components in a stripper 9. The stripper effluent is a gaseous stream of secondary components (W/ACH/FA, i.e., water/acetaldehyde/formaldehyde) which leaves the system.

A further difference to the process scheme of FIG. 1 is that the top part of the last vacuum dewatering column 10 has an outlet for an aqueous vapor stream loaded with secondary components. Furthermore, the main product of the monoethylene glycol purifying distillation column 6 is now withdrawn as a sidestream and an overhead stream from the monoethylene glycol purifying distillation column 6 is recycled into the middle section of the last vacuum dewatering column 10.

Figure 3:
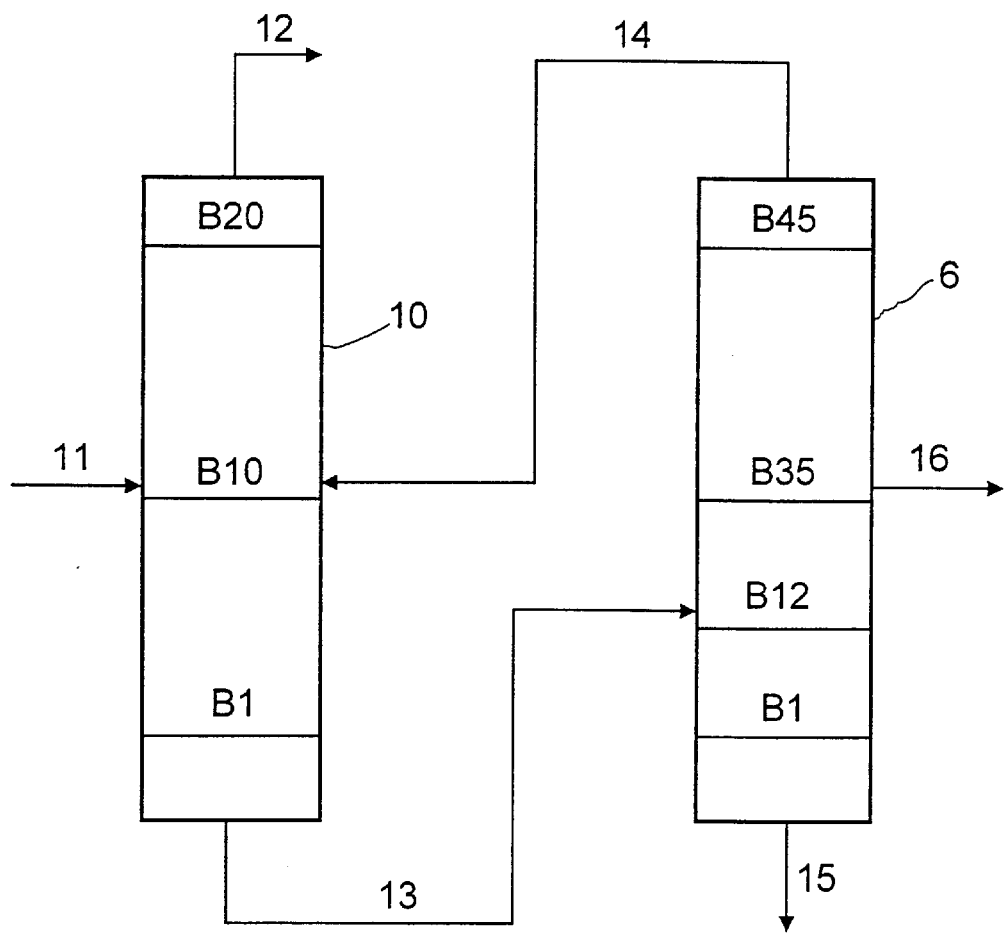
FIG. 3 shows an illustrative example of a process of the invention, featuring an outlet for secondary components as overhead stream of a vacuum dewatering column.

FIG. 3 shows an example of an inventive outlet created in the top region of the last vacuum dewatering column 10. The vacuum dewatering column 10 is supplied onto the $10^{th}$ (B10) plate with a stream 11 which, via the vacuum dewatering column 10, which is equipped with 20 bubble cap plates, is separated into an overhead stream 12 and a bottom stream 13. The bottom stream 13 is introduced onto the $12^{th}$ plate (B12) of a monoethylene glycol purifying distillation column 6 having 45 bubble cap plates; a high purity monoethylene glycol stream 16 is withdrawn via a sidestream takeoff from the $35^{th}$ plate (B35). The overhead stream 14 from the monoethylene glycol purifying distillation column 6 is returned onto the $10^{th}$ plate (B10) of the last vacuum dewatering column 10. The bottom stream 15 from the monoethylene glycol purifying distillation column 6 is fed to the further purifying distillation columns. The composition of the streams 11–16 is recited below in Table 1. It can be seen in particular that the concentration of secondary components, especially acetaldehyde, formaldehyde and glycolaldehyde, decreases significantly from the feed 11 to the last vacuum dewatering column 10 to the sidestream takeoff 16 of the monoethylene glycol purifying distillation column 6 while at the same time the corresponding UV transmission at 220 nm and also at 275 nm increases.

TABLE 1

| Stream No. | | 11 Aqueous glycol-containing column feed | 12 Aldehyde-containing wastewater | 13 Dewatered glycol stream | 14 Recycling of aldehyde-containing glycol | 15 Bottom stream of monoethylene glycol purifying distillation | 16 Monoethylene glycol sidestream takeoff |
|---|---|---|---|---|---|---|---|
| Total stream | kg/h | 2,500 | 0.080 | 2.480 | 0.062 | 0.730 | 1.690 |
| Temperature | ° C. | 120 | 70 | 160 | 144 | 175 | 145 |
| | | liquid | liquid | liquid | liquid | liquid | liquid |
| Water | % by weight | 3.19 | 99.95 | 0.01 | 0.38 | 0.00 | 0.00 |
| Monoethyl-ene glycol | % by weight | 79.95 | 0.01 | 83.01 | 99.59 | 42.33 | 99.98 |
| Diethylene glycol | % by weight | 13.40 | 0.00 | 13.50 | 0.00 | 45.83 | 0.02 |
| Triethylene glycol | % by weight | 2.87 | 0.00 | 2.89 | 0.00 | 9.83 | 0.00 |
| Tetraethylene glycol | % by weight | 0.59 | 0.00 | 0.59 | 0.00 | 2.01 | 0.00 |
| Acetaldehyde | % by weight | 0.00 | 0.02 | 0.00 | 0.00 | 0.00 | 0.00 |
| Formaldehyde | % by weight | 0.00 | 0.01 | 0.00 | 0.01 | 0.00 | 0.00 |
| Glycolaldehyde | % by weight | 0.00 | 0.01 | 0.00 | 0.03 | 0.00 | 0.00 |
| Acetaldehyde | weight ppm | 5 | 157 | 0 | 10 | 0 | 0 |
| Formaldehyde | weight ppm | 7 | 144 | 5 | 89 | 0 | 3 |
| Glycolaldehyde | weight ppm | 6 | 78 | 10 | 262 | 3 | 4 |
| Total | | 100.00 | 100.00 | 100.00 | 100.00 | 100.00 | 100.00 |
| UV transmission at 220 nm | % | 68.71 | 53.95 | 69.18 | 64.42 | 22.54 | 88.92 |
| UV transmission at 275 nm | % | 96.61 | 83.56 | 94.84 | 93.76 | 80.54 | 98.86 |

Figure 4:
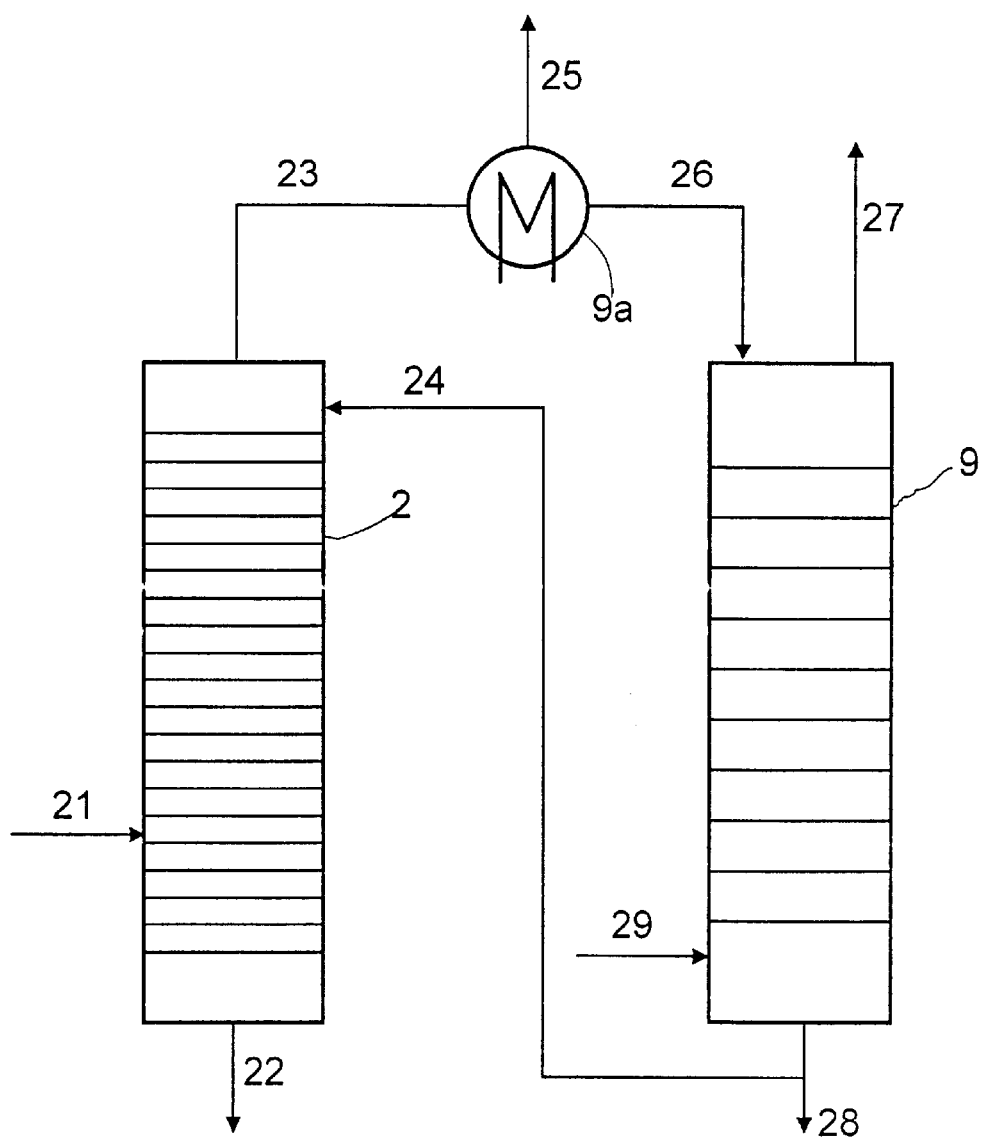
FIG. 4 shows an illustrative example of a process of the invention, featuring a pressure dewatering column with a stripping section and an outlet for secondary components as overhead stream and also subsequent concentrating in a partial condenser and a stripper.

FIG. 4 shows an example of the inventive modification of a pressure dewatering column 2 with stripping section and also with a stripper 9 for concentrating the secondary components prior to their being removed from the system. The feed 21 of the glycol-containing stream to be separated is on the 5$^{th}$ plate of a pressure dewatering column 2 possessing 20 bubble cap plates. Its overhead stream 23 is, after partial condensation, introduced as stream 26 onto a stripper 9 possessing 10 bubble cap plates and stripped free of secondary components by countercurrent steam 29. The gaseous streams 25 and 27 containing secondary components are removed from the system. Part 24 of the bottom effluent of stripper 9 forms the reflux into the dewatering column 2. The composition of the streams 21–29 is recited in Table 2a for a process of the invention. For comparison, the composition of the streams 21–29 is recited in Table 2b for a process according to the prior art, i.e., with pressure dewatering column without stripping section and without stripper.

TABLE 2a

| Stream No. | | 21 Hydrolysis reactor effluent | 22 Column 2 product | 23 Column 2 vapor | 24 Reflux | 25 Condenser exit gas | 26 Condensate | 27 Stripper exit gas | 28 Recycle water | 29 Stripping steam |
|---|---|---|---|---|---|---|---|---|---|---|
| Total stream | kg/h | 124.38 | 84.46 | 51.891 | 11.975 | 0.8 | 51.091 | 1.531 | 39.14 | 1.5 |
| Temperature | ° C. | 235 | 183 | 178 | 178 | 178 | 178 | 178 | 178 | 200 |
| | | liquid | liquid | gaseous | liquid | gaseous | liquid | gaseous | liquid | gaseous |

TABLE 2a-continued

| Stream No. | | 21 Hydrolysis reactor effluent | 22 Column 2 product | 23 Column 2 vapor | 24 Reflux | 25 Condenser exit gas | 26 Condensate | 27 Stripper exit gas | 28 Recycle water | 29 Stripping steam |
|---|---|---|---|---|---|---|---|---|---|---|
| Water | % by weight | 77.58 | 67.00 | 99.97 | 99.98 | 99.76 | 99.97 | 99.80 | 99.98 | 100.00 |
| Monoethylene glycol | % by weight | 18.30 | 26.96 | 0.00 | 0.00 | 0.00 | 0.00 | 0.00 | 0.00 | 0.00 |
| Diethylene glycol | % by weight | 3.25 | 4.79 | 0.00 | 0.00 | 0.00 | 0.00 | 0.00 | 0.00 | 0.00 |
| Triethylene glycol | % by weight | 0.71 | 0.20 | 0.00 | 0.00 | 0.00 | 0.00 | 0.00 | 0.00 | 0.00 |
| Tetraethylene glycol | % by weight | 0.14 | 0.00 | 0.00 | 0.00 | 0.00 | 0.00 | 0.00 | 0.00 | 0.00 |
| Acetaldehyde | % by weight | 0.00 | 0.00 | 0.01 | 0.00 | 0.14 | 0.00 | 0.11 | 0.00 | 0.00 |
| Formaldehyde | % by weight | 0.01 | 0 | 0.02 | 0.02 | 0.09 | 0.02 | 0.09 | 0.02 | 0.00 |
| Acetaldehyde | weight ppm | 26 | 24 | 64 | 10 | 1434 | 43 | 1071 | 10 | 0 |
| Formaldehyde | weight ppm | 94 | 100.00 | 231 | 192 | 935 | 219 | 934 | 192 | 0 |
| Total | | 100.00 | 100.00 | 100.00 | 100.00 | 100.00 | 100.00 | 100.00 | 100.00 | 100.00 |
| Water | g/h | 96,497.1 | 56,588.2 | 51,875.7 | 11,972.6 | 798.1 | 51,077.6 | 1527.9 | 39,132.1 | 1500.0 |
| Monoethylene glycol | g/h | 22,765.3 | 22,770.1 | 0.0 | 0.0 | 0.0 | 0.0 | 0.00 | 0.0 | 0.0 |
| Diethylene glycol | g/h | 4046.5 | 4047.3 | 0.0 | 0.0 | 0.0 | 0.0 | 0.0 | 0.0 | 0.0 |
| Triethylene glycol | g/h | 883.5 | 883.7 | 0.0 | 0.0 | 0.0 | 0.0 | 0.0 | 0.0 | 0.0 |
| Tetraethylene glycol | g/h | 172.8 | 172.8 | 0.0 | 0.0 | 0.0 | 0.0 | 0.0 | 0.0 | 0.0 |
| Acetaldehyde | g/h | 3.2 | 0.0 | 3.3 | 0.1 | 1.6 | 2.2 | 1.6 | 0.4 | 0.0 |
| Formaldehyde | g/h | 11.7 | 2.0 | 12.0 | 2.3 | 1.4 | 11.2 | 1.4 | 7.5 | 0.0 |

TABLE 2b

| Stream No. | | 21 Hydrolysis reactor effluent | 22 Column 2 product | 23 Column 2 vapor | 24 Reflux | 25 Condenser exit gas | 26 Condensate | 27 Stripper exit gas | 28 Recycle water | 29 Stripping steam |
|---|---|---|---|---|---|---|---|---|---|---|
| Total stream | kg/h | 124.42 | 84.47 | 51.925 | 11.975 | 0.8 | 51.125 | | 39.15 | 0 |
| Temperature | ° C. | 235 | 183 | 178 | 178 | 178 | 178 | 0 | 178 | |
| | | liquid | liquid | gaseous | liquid | gaseous | liquid | | liquid | |
| Water | % by weight | 77.58 | 67.00 | 99.98 | 99.98 | 99.78 | 99.98 | | 99.98 | |
| Monoethylene glycol | % by weight | 18.30 | 26.90 | 0.00 | 0.00 | 0.00 | 0.00 | | 0.00 | |
| Diethylene glycol | % by weight | 3.25 | 4.79 | 0.00 | 0.00 | 0.00 | 0.00 | | 0.00 | |
| Triethylene glycol | % by weight | 0.71 | 1.05 | 0.00 | 0.00 | 0.00 | 0.00 | | 0.00 | |
| Tetraethylene glycol | % by weight | 0.14 | 0.20 | 0.00 | 0.00 | 0.00 | 0.00 | | 0.00 | |
| Acetaldehyde | % by weight | 0.00 | 0.00 | 0.01 | 0.00 | 0.15 | 0.00 | | 0.00 | |
| Formaldehyde | % by weight | 0.01 | 0.01 | 0.02 | 0.02 | 0.07 | 0.02 | | 0.02 | |
| Acetaldehyde | weight ppm | 26 | 3 | 67 | 45 | 1508 | 45 | 0 | 45 | |
| Formaldehyde | weight | 94 | 55 | 173 | 165 | 701 | 165 | 0 | 165 | |

TABLE 2b-continued

| Stream No. | | 21 Hydrolysis reactor effluent | 22 Column 2 product | 23 Column 2 vapor | 24 Reflux | 25 Condenser exit gas | 26 Condensate | 27 Stripper exit gas | 28 Recycle water | 29 Stripping steam |
|---|---|---|---|---|---|---|---|---|---|---|
| aldehyde | ppm | | | | | | | | | |
| Total | | 100.00 | 100.01 | 100.00 | 100.00 | 100.00 | 100.00 | | 100.00 | |
| Water | g/h | 96,528.1 | 56,594.9 | 51,912.5 | 11,972.5 | 798.2 | 51,114.3 | | 39,141.8 | |
| Monoethylene glycol | g/h | 22,772.6 | 22,772.8 | 0.0 | 0.0 | 0.0 | 0.0 | | 0.0 | |
| Diethylene glycol | g/h | 4047.8 | 4047.8 | 0.0 | 0.0 | 0.0 | 0.0 | | 0.0 | |
| Triethylene glycol | g/h | 883.8 | 883.8 | 0.0 | 0.0 | 0.0 | 0.0 | | 0.0 | |
| Tetraethylene glycol | g/h | 172.8 | 172.8 | 0.0 | 0.0 | 0.0 | 0.0 | | 0.0 | |
| Acetaldehyde | g/h | 3.2 | 0.3 | 3.5 | 0.5 | 1.2 | 2.3 | | 1.7 | |
| Formaldehyde | g/h | 11.7 | 4.6 | 9.0 | 2.0 | 0.6 | 8.4 | | 6.5 | |

The process of the invention provides for a product stream 22 being obtained from the first pressure dewatering column 2 which has a lower level of impurities (0.0 g/h of acetaldehyde and 2.0 g/h of formaldehyde) than the prior art (0.3 g/h of acetaldehyde and 4.6 g/h of formaldehyde).

The secondary components removed from the system by the process of the invention are 1.1 g/h of acetaldehyde and 0.7 g/h of formaldehyde in stream 25 and 1.6 g/h of acetaldehyde and 1.4 g/h of formaldehyde in stream 27 compared with only 1.2 g/h of acetaldehyde and 0.6 g/h of formaldehyde in stream 25 according to the prior art process.

We claim:

1. In a process for the distillative recovery of monoethylene glycol from the hydrolysis product of ethylene oxide which comprises
   (a) a pressure dewatering stage which is conducted in:
      one pressure dewatering column or a battery of pressure dewatering columns,
      wherein the hydrolysis product is fed to the one, or to a first of the battery of, pressure dewatering column(s) at a feeding point between the head and the base of said pressure dewatering column,
   (b) a subsequent vacuum dewatering stage, and
   (c) a purifying distillation of the dewatered monoethylene glycol recovered from the vacuum dewatering stage,
   the improvement which comprises:
      withdrawing an aqueous stream which comprises monoethylene glycol in a concentration below 1% by weight, and additionally medium boilers and low boilers, either
      i) as a side stream from a single vacuum dewatering column which is utilized in stage (b), or
      ii) as an overhead stream from a second of two vacuum dewatering columns which are utilized in stage (b),
   and, optionally after further workup, removing the withdrawn stream from the process.

2. The process of claim 1, wherein the concentration of monoethylene glycol in the withdrawn aqueous stream is below 0.1% by weight.

3. The process of claim 1, wherein an overhead stream of monoethylene glycol is removed from the purifying distillation, and the overhead stream is returned into the one, or the last of the, vacuum dewatering column(s), and purified monoethylene glycol is withdrawn from the purifying distillation as a side stream.

4. The process of claim 3, wherein the overhead stream of monoethylene glycol which is removed from the purifying distillation is returned into a middle section of the one, or the last of the, vacuum dewatering column(s).

5. The process of claim 3, wherein the overhead stream of monoethylene glycol which is removed from the purifying distillation amounts to from 1 to 10% of the monoethylene glycol side stream and/or the monoethylene glycol side stream is withdrawn from the purifying distillation at a distance from the top of the distillation column of from 1 to 10 separating stages.

6. The process of claim 5, wherein the distance is from 3 to 6 separating stages.

7. The process of claim 1, wherein said at least one or first vacuum dewatering column has a base-of-column temperature which does not exceed 220° C.

8. The process of claim 7, wherein the base-of-column temperature is within the range from 120° C. to 200° C.

9. The process of claim 8, wherein the base-of-column temperature is within the range from 160° C. to 180° C.

10. The process of claim 1, wherein the one, or the first of the battery of, pressure dewatering column(s) has a stripping section with at least one separating stage, and wherein an overhead stream is removed from said one or first pressure dewatering column, and a portion of said removed overhead stream is withdrawn from the process.

11. The process of claim 10, wherein the stripping section of said one or first pressure dewatering column has from 2 to 10 separating stages.

12. The process of claim 11, wherein the stripping section of said one or first pressure dewatering column has from 3 to 6 separating stages.

13. The process of claim 10, wherein the one or first pressure dewatering column has a temperature below the feed point of above 80° C., and the pressure in the stripping section is not less than 1 bar.

14. The process of claim 13, wherein the temperature below the feed point is within the range from 100° C. to 250° C.

15. The process of claim 13, wherein the temperature below the feed point is within the range from 115° C. to 230° C.

16. The process of claim 13, wherein the pressure in the stripping section is within the range from 2 to 30 bar.

17. The process of claim 10, wherein the overhead stream which is removed from the one or the first pressure dewatering column is introduced into a partial condenser and/or stripper, and a gaseous stream which is obtained from the condenser and/or the stripper is removed from the process.

18. The process of claim 17, wherein the stripper is a steam stripper.

19. The process of claim 17, wherein the partial condenser and the stripper are operated at a temperature above 90° C.

20. The process of claim 17, wherein the operating temperature of the partial condenser and the stripper is at from 120° C. to 250° C.

* * * * *

UNITED STATES PATENT AND TRADEMARK OFFICE
CERTIFICATE OF CORRECTION

PATENT NO.    : 6,605,192 B1  
DATED         : August 12, 2003  
INVENTOR(S)   : Theis et al.

Page 1 of 1

It is certified that error appears in the above-identified patent and that said Letters Patent is hereby corrected as shown below:

Title page,
Item [86], "PCT/EP98/06968" should be -- PCT/EP99/06968 --.
Item [57], ABSTRACT,
Line 2, "hydrolysis, product" should be -- hydrolysis product --;
Line 6, "contains-monoethylene" should be -- contains monoethylene --.

Signed and Sealed this

Thirtieth Day of September, 2003

JAMES E. ROGAN
*Director of the United States Patent and Trademark Office*